United States Patent [19]

Madison et al.

[11] Patent Number: 5,284,944

[45] Date of Patent: Feb. 8, 1994

[54] IMPROVED SYNTHESIS OF 1,4,7-TRIAZACYCLONONANE

[75] Inventors: Steven A. Madison, Valley Cottage, N.Y.; David J. Batal, Secaucus, N.J.

[73] Assignee: Lever Brothers Company, Division of Conopco, Inc., New York, N.Y.

[21] Appl. No.: 906,782

[22] Filed: Jun. 30, 1992

[51] Int. Cl.⁵ ............................................ C07D 255/02
[52] U.S. Cl. .................................. 540/474; 540/465
[58] Field of Search ............................ 540/474, 465

[56] References Cited

FOREIGN PATENT DOCUMENTS

| | | |
|---|---|---|
| 0375333 | 6/1990 | European Pat. Off. ............ 540/474 |
| WO86/02352 | 4/1986 | PCT Int'l Appl. ................. 540/474 |
| 1529150 | 10/1978 | United Kingdom . |

OTHER PUBLICATIONS

Zhana et al. Chemical Abstracts vol. 108, 1988, Abstract 94530w.
Organic Syntheses, 58, pp. 86-98 (1978).
Luk'yanenko et al, Zhurnal Organ. Khimii, 25, 8, pp. 1776-1784 (Dec. 30, 1989) with English translation pp. 1537-1544 (Aug. 1990).
Luk'yanenko et al, Zhurnal Organ. Khimii, 23 (3), pp. 660-662 (Jun. 3, 1986 with English translation pp. 598-599 (Mar. 1987).
Searle and Geue, Aust. J. Chem. 37, pp. 959-970 (1984).
Qian et al, Tetrahedron Letters, 31 (45), pp. 6469-6472 (1990).
Biernat and Luboch, Tetrahedron Letters, 40 (10), pp. 1927-1929 (1984).
Buttafava et al., Inorg. Chem., 25, pp. 1456-1461 (1986).
McAuley et al., Inorg. Chem., 23, pp. 1938-1943 (1984).
Schneider and Busch, Chem. Ber., 119, pp. 747-750 (1986).
Bogatsky et al, Communications, pp. 136-138 (Feb. 1984).
Chavez and Sherry, J. Org. Chem., 54, pp. 2990-2992 (1989).
Pilichowski et al, Tetrahedron Letters, 41 (10), at pp. 1961.

*Primary Examiner*—Mukund J. Shah
*Assistant Examiner*—E. C. Ward
*Attorney, Agent, or Firm*—Milton L. Honig

[57] ABSTRACT

An improved process is described for obtaining triazacyclononanes, esepcially 1,4,7-trimethyl-1,4,7-triazacyclononame. The first step involves reacting diethylenetriamine (DET) with a sulfonylation agent to form a sulfonamidated DET, in an aqueous medium with an inorganic base. In a second step, but preferably within the same reactor vessel without isolating intermediates, the sulfonamidated DET aqueous mixture is contacted with an aprotic organic solvent in the presence of a cyclizing unit such as ethylene glycol ditosylate or ethylene dibromide, thereby resulting in a cyclized sulfonamidated triamine compound. Thereafter the protecting groups are removed and the amine is alkylated, preferably within a single reaction vessel without isolation of intermediates.

13 Claims, No Drawings

IMPROVED SYNTHESIS OF 1,4,7-TRIAZACYCLONONANE

BACKGROUND OF THE INVENTION

1. Field of the Invention

The invention concerns an improved synthesis of triazacyclononane rings, especially of 1,4,7-trimethyl-1,4,7-triazacyclononane useful as a ligand with manganese in a catalyst for bleaching.

2. The Related Art

Recently a series of manganese complexes have been identified as exceptionally active for bleaching fabrics. The unusual catalytic performance of the complex can at least partially be attributed to its unusual ligand 1,4,7-trimethyl-1,4,7-triazacyclononane, hereinafter referred to by its acronym, MeTACN. The catalysts have the general structure:

A significant economic problem with the catalyst was that of the cost of the ligand. Synthesis of MeTACN has been set forth principally by Richman and Atkins in *Organic synthesis,* 58, pp. 86–98 (1978). Additional important related references are as follows Luk'yanenko et. al., *Khim. Geterotsikl. Soedin.* 23 (3), pp. 401–404 (1990); Luk'yanenko et. al., *Zhurnal Organ. Khimii,* 25, 8, pp. 1776–1784 (Dec. 30, 1989) with translation pp. 1537–1544 (August 1990); Luk'yanenko et. al., *Zhurnal Organ. Khimii,* 23 (3). pp. 660–662 (Jun. 3, 1986) with English translation pp. 598–599 (March 1987); Searle and Geue, *Aust. J. Chem.* 37, pp. 959–970 (1984); Qian et. al., *Tetrahedron Letters.* 31 (45), pp. 6469–6472 (1990); Biernat and Luboch, *Tetrahedron Letters,* 40 (10), pp. 1927–1929 (1984); Buttafava et. al., *Inorg. Chem.* 25, pp. 1456–1461 (1986); McAuley et. al., *Inorg. Chem.,* 23, pp. 1938–1943 (1984); Schneider and Busch, *Chem. Ber.* 119, pp. 747–750 (1986); Bogatsky et. al., *Communications,* pp. 136–138 (February 1984); and Chavez and Sherry, *J. Org. Chem.,* 54, pp. 2990–2992 (1989). Pilichowski et. al., *Tetrahedron Letters.* 41 (10), at pp. 1961 (right column) describes tosylation of diethylenetriamine in an aqueous base. Relevant patent literature includes EP 0 375 333 (Tanis et. al.) and WO 86/02352 (Sherry).

While the Richman and Atkins approach to MeTACN is satisfactory for small scale preparations, it is not amenable to large scale production. Furthermore, the known process consists of six synthetic steps and a waste stream (solvents not recyclable) which renders the route unattractive. Safety issues also arise with the known art. Thus, an improved procedure was found to be imperative.

Accordingly, it is an object of the present invention to provide an improved synthesis of triazacyclononanes involving a reduction in the number of steps including reducing the number of intermediates required to be isolated.

Another object of the present invention is to provide an improved synthesis of triazacyclononanes which avoids or reduces undesirable solvents such as pyridine and DMF, as well as other solvents that do not allow for recycling and may pose a potential worker safety problem.

Still another object of the present invention is to provide an improved synthesis of triazacyclononanes that avoids use of boiling hydrobromic and acetic acids which are both impractical and dangerous.

A further object of the present invention to provide an improved synthesis of triazacyclononanes wherein various reaction treatments can be conducted in a single reactor without isolation of intermediates.

A still further object of the present invention is to provide an improved synthesis of triazacyclononanes that, for the most part, can be conducted in water to avoid waste solvent and that improves upon product yield.

These and other objects of the present invention will become more readily apparent by consideration of the following summary, detailed description and examples.

SUMMARY OF THE INVENTION

A process is described for preparing a triazacyclononane of the structure:

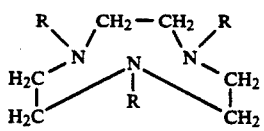

wherein R is a radical selected from the group consisting of hydrogen, methyl, ethyl and propyl.

The steps of the process include:

(i) reacting 1,4,7-diethylenetriamine with a compound of the formula R'-L wherein R' is selected from the group consisting of aryl, benzyl and alkyl and L is a halosulfonyl group, with a base in water to form a sulfonamidated diethylenetriamine;

(ii) contacting the sulfonamidated diethylenetriamine held in an aqueous medium with an aprotic organic solvent in the presence of a cyclizing unit selected from the group consisting of ethylene glycol disulfonylate, ethylene dihalide and diacetyl glycol, and a further amount of a base to deprotonate the sulfonamidated diethylenetriamine to obtain a sulfonamidated cyclized triamine compound; and (iii) removing sulfonyl protecting groups from the cyclized sulfonamidated triamine compound.

DETAILED DESCRIPTION

Now a simplified process for obtaining MeTACN and derivatives has been achieved through elimination and consolidation of known synthetic steps in combination with certain new process features. The Richman and Atkins preparation, which previously required at least six steps, has now been reduced to no more than four steps, and under an optimum procedure, to two steps. Flow diagrams for the known and the two improved syntheses are outlined below.

DET = 1,4,7-diethylenetriamine
TACN = 1,4,7-triazacyclononane
EGT = ethylene glycol ditosylate
Ts = tosyl Richman and Atkins Type Preparation of MeTACN

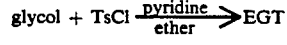

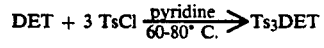

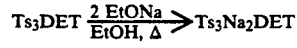

-continued

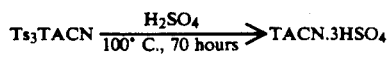

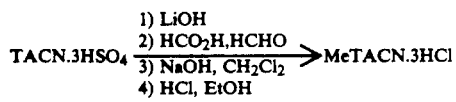

Improved Synthesis of MeTACN

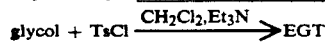

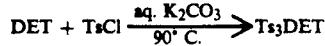

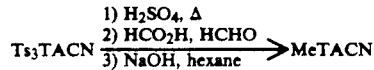

Two-Step Synthesis of MeTACN

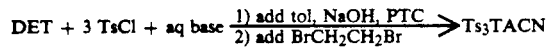

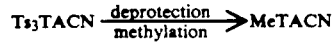

First, the key aspect of the invention is that the starting reagent 1,4,7-diethylenetriamine (DET) is reacted with a sulfonyl chloride in an aqueous medium rather than an organic one. Ordinarily the known art utilizes an organic amine such as pyridine or triethylamine to accomplish sulfonamidation. Here an aqueous system eliminates the need for removal of the organic solvent which thereby avoids handling of such solvent and permits direct use of the sulfonamidated DET in the same vessel for the next reaction which is cyclization.

A water-soluble base is utilized in combination with the aqueous medium to achieve sulfonamidation. Inorganic basic salts are preferred, especially sodium hydroxide. Advantageously, pH should be maintained between about 8 and about 12. Other suitable bases include the alkali carbonates and bicarbonates such as potassium carbonate and sodium bicarbonate. The necessary level of base will be in an amount sufficient to remove any acidic hydrohalide generated in the sulfonamidation reaction. Although sulfonamidation will proceed to some extent at room temperature, preferably the aqueous medium should be heated to greater than 50° C., preferably from 65° C. to 100° C., optimally between 80° C. and 95° C..

Thus, the invention is further distinguished by conducting sulfonamidation in a monophasic aqueous system wherein a solid sulfonyl chloride (at room temperature) is caused to be melted/dispersed through contact with the hot water. Ordinarily the art would operate at relatively low temperatures utilizing either an organic solvent or at least a biphasic aqueous/organic system to cold temperature dissolve the solid sulfonyl halide.

Sulfonamidation reagents will have the general formula R'-L wherein R' may be selected from the group consisting of aryl, benzyl and alkyl radicals, while L is a halosulfonyl group, especially a sulfonyl chloride. Suitable sulfonamidation reagents are aromatic sulfonyl chlorides such as the benzene-, toluene-, p-nitrobenzene- and p-bromobenzene- sulfonyl chlorides; and alkane sulfonyl chlorides such as methane sulfonyl chloride.

Cyclization of sulfonamidated DET is conducted in a biphasic reaction medium consisting of an organic solvent and water. Suitable organic solvents include methylene chloride, chloroform, diethylether, THF, benzene, xylene, toluene, hexane, petroleum ether and combinations thereof. Most preferred are xylene and toluene because of their low toxicity and boiling point. A base such as sodium hydroxide is dissolved in the aqueous phase. Best yields are obtained through use of a cationic phase-transfer catalyst (PTC). A PTC usually is of the structural formula:

wherein R" may be selected from the group consisting of aryl, benzyl, phenyl, alkyl; and X will be an anion selected from the group consisting of iodide, bromide, chloride, bisulfate, sulfate, phosphate and organic moieties attached to the aforementioned anions. Most preferred as the PTC is tricaprylmethylammonium chloride. Compounds other than quaternary ammonium salts may also be useful, for example, the crown ethers or linear polyethers.

Cyclization of the sulfonamidated DET may be achieved through a cyclizing unit selected from the group consisting of diorganosulfonylate (e.g. ditosylate), ethylene dibromide, ethylene dichloride and diacetyl glycol. Each of the aforementioned units provides the two-carbon homologating agent for closure of the ring.

In the four-step procedure, cyclization with ethylene glycol ditosylate (EGT) affords a tritosylated 1,4,7-triazacyclononane (Ts₃TACN) of high purity in about 75% yield. The major drawback of this cyclization concerns the poor space yield of product (ca. 37 grams product per liter of solvent). Preferable is the use of ethylene dibromide (EDB), dichloroethane or diacetyl glycol. With EDB, the cyclic product forms at a rate comparable to that with EGT. The yield and purity is also comparable to that derived from EGT chemistry. Replacement of EGT with EDB is advantageous since the latter, being a liquid, facilitates manipulation in manufacturing and is of lower cost. EDB also has the advantage that it may be added in two or more portions to the cyclization step compared with the necessary slow addition of EGT over a period of several hours. Moreover, sulfonamidation and cyclization may be conducted in the same vessel without isolation of intermediates when utilizing EDB. Thus, the first of the two-step synthesis will achieve under a one-vessel protocol an amount of Ts₃TACN in about 75% yield. Deprotection/methylation is conducted in a separate vessel from that of the cyclization step.

Deprotection of the sulfonamidated cyclized DET is achieved by contact with an inorganic acid. Illustrative is sulfuric acid which achieves complete deprotection of Ts₃TACN at about 140° C. in 5-6 hours. Thereafter, increasing the pH of the deprotected mixture to pH 14 provides a fine sulfate slurry containing free triazacyclononane.

Filtration of the deprotected mixtures can be extremely difficult and extraction with various solvents provides only low yields of TACN. According to the present invention, the problem has been circumvented by neutralizing the deprotection mixture followed by in situ methylation with formic acid and formaldehyde.

After methylation becomes complete, the pH is adjusted to 14 to provide a slurry of the product.

According to the present invention, it has also been found that the aforementioned slurries can be rectified through the use of a $C_5$-$C_8$ hydrocarbon which may include pentane, hexane, heptane, octane, cyclopentane, cyclohexane, cycloheptane, cyclooctane, toluene, xylene and combinations thereof. Preferably, the rectifying solvent is hexane. Through the addition of hexane the slurries of finely suspended TACN can be separated to allow forming a semi-crystalline precipitate which can easily be removed by filtration; the precipitate is a mixture of by-products. Alkylated TACN, such as MeTACN can then be recovered as a near colorless liquid.

In accordance with the present invention, it was particularly surprising that still protected sulfonamidated triamine compound, e.g. $Ts_3$TACN could be directly alkylated in situ without first isolation of the deprotected TACN ring.

The following examples will more fully illustrate the embodiments of this invention. All parts, percentages and proportions referred to herein and in the appended claims are by weight unless otherwise indicated.

EXAMPLE 1

The following experimental procedure outlines the four-step method for obtaining MeTACN.

Step 1: Ethylene Glycol di-o-tosylate (EGT)

In a 5-L three-necked round bottomed flask equipped with a mechanical stirrer and a reflux condenser were placed 50.33 g (0.81 mol) of ethylene glycol in 2 liters of methylene chloride. Triethylamine (338.7 mL, 3 eq) was added. The mixture was stirred at 0° C. for 7 hours and was then placed in a 0° C. refrigerator for 14 hours. TLC analysis showed glycol ditosylate and a small amount of unreacted TsCl (slightly higher $R_f$ value (ether, silica gel). The precipitated triethylamine hydrochloride was filtered from the reaction. The filtrate was washed with 2500 mL of 1 N hydrochloric acid. The organic phase was separated, dried over $Na_2SO_4$, and concentrated to give a white crystalline material. Drying under vacuum (40° C.) gave 251.20 g (84%) of glycol ditosylate as a free-flowing white crystalline material. mp 117°-120° C.

Step 2: Tritoluenesulfonyldiethylenetriamine ($Ts_3$-DET)

In a 5-L three-necked round bottomed flask equipped with a mechanical stirrer and a reflux condenser were placed 514.4 g (3.72 mol) of anhydrous potassium carbonate in 4.4 L of milli-Q water. The mixture was stirred vigorously and 120.0 g (1.16 mol) of diethylenetriamine were added all at once. Solid TsCl (665.2 g, 3 eq) was added in portions over a 20-minute period. A slight warming was noted which after 0.5 hours led to an internal reaction temperature of 55° C. This exothermicity persisted for 2.5 hours. The reaction mixture was heated (with a mantle) to an internal temperature of 80°-84° C. for 1.5 hours. TLC analysis of the slurry (small amount of the solid dissolved in acetone) showed only $Ts_3$-DET and no TsCl (ether, silica gel). The reaction was allowed to cool to room temperature and was filtered. The product was washed with water and dried under vacuum at 55° C. to yield 587.2 g (89%) of $Ts_3$-DET as a white granular solid. m.p. 170°-174° C.

Step 3: Tritosyltriazacyclononane ($Ts_3$TACN)

In a 12-L three-necked round bottomed flask equipped with a mechanical stirrer and a reflux condenser were placed 216.0 g (0.38 mol) of $Ts_3$-DET in 3.6 L of toluene. The resulting white slurry was stirred vigorously and a solution of 33.6 g (2.2 eq) of sodium hydroxide in 700 mL of milli-Q water was added followed by 38 mL (0.1 eq) of a 1.0M solution of tetrabutylammonium hydroxide in water. The reaction mixtures was heated at 90° for 0.5 hours. Ethylene glycol ditosylate (crude material, 141.4 g, 1 eq) was then added over a 6 hour period (ca. 3.9 g portions every 10 minutes). At the end of the addition, TLC analysis showed predominant formation of $Ts_3$-TACN. The reaction mixture was heated for an additional 4 hours at 90° C. and was then allowed to cool to room temperature while stirring overnight (for about 6 hours). A large white precipitate formed in the reaction which was filtered and washed with water. This material was dried (50° C., 12 hours) to a constant weight of 171.5 g (76%). The product was white and granular in appearance: mp 205°-211° C., TLC one spot, 1H NMR and IR data in accord with the desired structure. Concentration of the toluene solution gave 60 g of a light orange tacky material (even after vacuum drying at 50° C.). Although TLC and 1H NMR data showed $Ts_3$-TACN to be the major component, the material was difficult to handle.

Step 4: 1,4,7-Trimethyl-1,4,7-triazacyclononane (MeTACN)

To a magnetically stirred 500-mL flask containing 106 mL of concentrated sulfuric acid and 19 ml of milli-Q water was added 100 g (0.17 mol) of $Ts_3$-TACN over a few minutes. A large portion of the $Ts_3$-TACN floated on top of the mixture. The reaction mixture was heated in a 140° C. oil bath. After stirring vigorously for 15 minutes, the material dissolved in the acid. Heating was continued for a total of 6 hours. A 5-L flask equipped with an overhead stirrer and a condenser was cooled to 0° C. and charged with 308 g of 50% NaOH and 125 mL of water. The alkaline solution was vigorously stirred and the sulfuric acid mixture was added through an addition funnel over a 45-minute period (conducted by transferring about 20 mL aliquots into the addition funnel). The resulting mixture was intended to have a pH of 7. the reaction was maintained at 0° C. and 225 mL of 37% formaldehyde and 225 mL of 88% formic acid were added sequentially. The mixture was heated to an internal temperature of 90° C. The evolution of $CO_2$ was moderate. The reaction was heated at this temperature for 14 hours. The reaction was cooled to 0° C. and 490 g of 50% NaOH was added over a 35-minute period through an addition funnel. The resulting slurry showed a pH of 14 (indicator paper). About 400 mL of hexane were added and the mixture was stirred for 2 minutes. The reaction mixture was filtered and the crystalline material on the grit was washed with an additional 150 mL of hexane. The organic phase of the mother liquor was separated and the aqueous portion was extracted with 200 mL of hexane. The combined extracts were dried over a small amount of $Na_2SO_4$, filtered, and concentrated to yield 25.34 g (88%) of MeTACN as a very light yellow liquid. The material was stored in a tightly-capped brown glass bottle at 0° C.

EXAMPLE 2

Hereunder is discussed the two-step process of the present invention. To obtain MeTACN in a two-vessel procedure.

Step 1: Tritosyl-1,4,7-Triazacyclononane (Ts₃TACN)

In a 5-L three-necked round bottomed flask equipped with a mechanical stirrer and a reflux condenser were placed 121.1 g (0.88 mol) of anhydrous potassium carbonate in 300 L of milli-Q water. The mixture was stirred vigorously and 27.4 g (0.27 mol) of diethylenetriamine were added all at once. Solid tosyl chloride (156.9 g, 3.1 eq) was added and the resulting mixture was heated for one hour at 90° C. The heating source was removed and 1.2 L of xylene, 95.6 g of sodium hydroxide (9 eq), 26.6 mL (0.1 eq) of a 1M solution of tetrabutylammonium hydroxide in water, and 40 mL (1.75 eq, 87.2 g) of ethylene dibromide were added sequentially. The reaction mixture was heated at 90° for 4 hours and a further 40 mL of ethylene dibromide were added. This was followed at 8 hours by an additional 40 ml EDB. The reaction was heated at 90° for another 18 hours and was then allowed to cool to room temperature. The resulting precipitate was filtered, washed with water, and dried under vacuum to give a constant weight of 119.3 g (75%) of a white granular material. TLC analysis indicated only Ts₃TACN: m.p. 203°-208° C.

Step 2: 1,4,7-Trimethyl-1,4,7-Triazacyclononane (MeTACN)

To a magnetically stirred 250-mL flask containing 50 mL (85 mol) of Ts₃TACN was added a solution consisting of 53 mL of concentrated sulfuric acid and 9.5 mL of milli-Q water. The reaction mixture was heated in a 140° C. oil bath. After stirring for 15 minutes, the material had dissolved in the acid (black in color). Heating was continued for a total of 6 hours. A 2-L flask equipped with an overhead stirrer and a condenser was cooled to 0° C. and charged with 154 of 50% NaOH and 62.5 mL of water. The alkaline solution was vigorously stirred and the sulfuric acid mixture was added over a 15-minute period. The resulting slurry was dark brown. Thereupon 112.5 ml of 37% formaldehyde and 112.5 mL of 88% formic acid were added sequentially. The mixture was heated to an internal temperature of 90° C. The evolution of CO₂ was moderate. The reaction was heated at this temperature for 14 hours. The reaction was cooled to 0° C. and 245 g of 50% NaOH was added over a 30-minute period. The resulting slurry showed a pH of 14 (test paper). About 200 mL of hexane were added and the mixture was stirred for 2 minutes. The reaction mixture was filtered and the remaining material on the frit was washed with hexane. The organic phase of the mother liquor was separated and the aqueous portion was extracted with 100 mL of hexane. The combined extracts were dried over Na₂SO₄, filtered, and concentrated to yield 7.9 g (55%) of MeTACN as a light yellow liquid.

The foregoing description and examples illustrate selected embodiments of the present invention. In light thereof, various modifications will be suggested to one skilled in the art, all of which are within the spirit and purview of this invention.

What is claimed is:

1. A process for preparing a triazacyclononane of the structure:

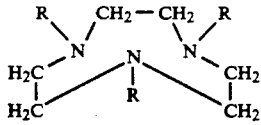

wherein R is a radical selected from the group consisting of hydrogen, methyl, ethyl and propyl the process comprising:

(i) reacting 1,4,7-diethylenetriamine with a compound of the formula R'-L wherein R' is selected from the group consisting of phenyl, benzyl and alkyl and L is a halosulfonyl group, with a base in water to form a sulfonamidated diethylenetriamine;

(ii) contacting the sulfonamidated diethylenetriamine held in a aqueous medium with an aprotic organic solvent to form a biphasic reaction medium in the presence of a cyclizing unit selected from the group consisting of ethylene glycol disulfonylate, ethylene dihalide and diacetyl glycol, and a further amount of a base to deprotonate the sulfonamidated diethylenetriamine to obtain a sulfonamidated cyclized triamine compound;

(iii) removing sulfonyl protecting groups from the cyclized sulfonamidated triamine compound to obtain a cyclized desulfonamidated traimine compound; and (iv) converting said cyclized desulfonamidated triamine compound to said triazacyclononane.

2. A process according to claim 1 wherein R'-L is selected from the group consisting of benzene sulfonyl chloride, toluene sulfonyl chloride, p-nitrobenzene sulfonyl chloride, p-bromobenzene sulfonyl chloride and methane sulfonyl chloride.

3. A process according to claim 1 wherein the base of step (i) is sodium hydroxide.

4. A process according to claim 2 wherein the base is selected from the group consisting of an alkali metal carbonate and bicarbonate.

5. A process according to claim 1 wherein the cyclizing unit is ethylene dibromide.

6. A process according to claim 1 wherein the water of step (i) is held at a temperature from 50° C. to 100° C.

7. A process according to claim 6 wherein R'-L is a solid at room temperature and is added to the water of step (i) so as to be melted therein thereby swiftly reacting with the diethylenetriamine.

8. A process according to claim 1 wherein a phase-transfer catalyst selected from the group consisting quaternary ammonium salts and polyethers is utilized in step (ii).

9. A process according to claim 1 wherein removal of protecting groups from the cyclized triamine is obtained by contact with an inorganic acid.

10. A process according to claim 1 wherein alkylation occurs in step (iv) through contact of the cyclized desulfonamidated triamine compound with formic acid and formaldehyde in an effective amount to achieve methylation on positions previously occupied by the sulfonyl protecting groups.

11. A process according to claim 10 wherein the sulfonamidated cyclized triamine of step (ii) is directly alkylated in situ.

12. A process according to claim 1 wherein step (i) and step (ii) are conducted in a single reactor vessel without isolation of any intermediates.

13. A process according to claim 12 wherein step (iii) involving removal of protecting groups form the cyclized triamine and methylation occur in a single vessel without isolation of any intermediates.

* * * * *